United States Patent [19]

Gazzi et al.

[11] Patent Number: 4,545,965
[45] Date of Patent: Oct. 8, 1985

[54] PROCESS OF SELECTIVE SEPARATION OF HYDROGEN SULFIDE FROM GASEOUS MIXTURES CONTAINING ALSO CARBON DIOXIDE

[75] Inventors: Luigi Gazzi, Milan; Carlo Rescalli, San Donato Milanese; Maria A. Scaramucci, Milan; Alessandro Ginnasi, San Donato Milanese, all of Italy

[73] Assignee: Snamprogetti, S.p.A., Milan, Italy

[21] Appl. No.: 602,736

[22] Filed: Apr. 23, 1984

Related U.S. Application Data

[63] Continuation of Ser. No. 215,169, Dec. 11, 1980, abandoned.

[30] Foreign Application Priority Data

Jul. 4, 1980 [IT] Italy .............................. 23241 A/80

[51] Int. Cl.⁴ .............................................. C01B 17/16
[52] U.S. Cl. ........................................ 423/229; 55/73
[58] Field of Search ................. 55/73; 423/226, 228, 423/229, 575

[56] References Cited

U.S. PATENT DOCUMENTS

| | | |
|---|---|---|
| 2,550,446 | 4/1951 | Blohm et al. . |
| 3,463,603 | 8/1969 | Freitas et al. . |
| 3,502,428 | 3/1970 | Gebein et al. . |
| 3,630,666 | 12/1971 | Kunkel . |
| 3,918,934 | 11/1975 | Kriebel . |
| 4,238,206 | 12/1980 | Hong . |
| 4,241,032 | 12/1980 | Werner et al. . |
| 4,242,108 | 12/1980 | Nicholas . |
| 4,259,301 | 3/1981 | Say . |

Primary Examiner—Bernard Nozick
Attorney, Agent, or Firm—Morgan, Finnegan, Pine, Foley & Lee

[57] ABSTRACT

There is disclosed a process for selectively separating hydrogen sulfide from gaseous mixtures which also contain carbon dioxide by chemical absorption with a substantially anhydrous solution of a tertiary amine, such as methyl diethanolamine, and an auxiliary organic solvent, such as sulfolane.

4 Claims, 1 Drawing Figure

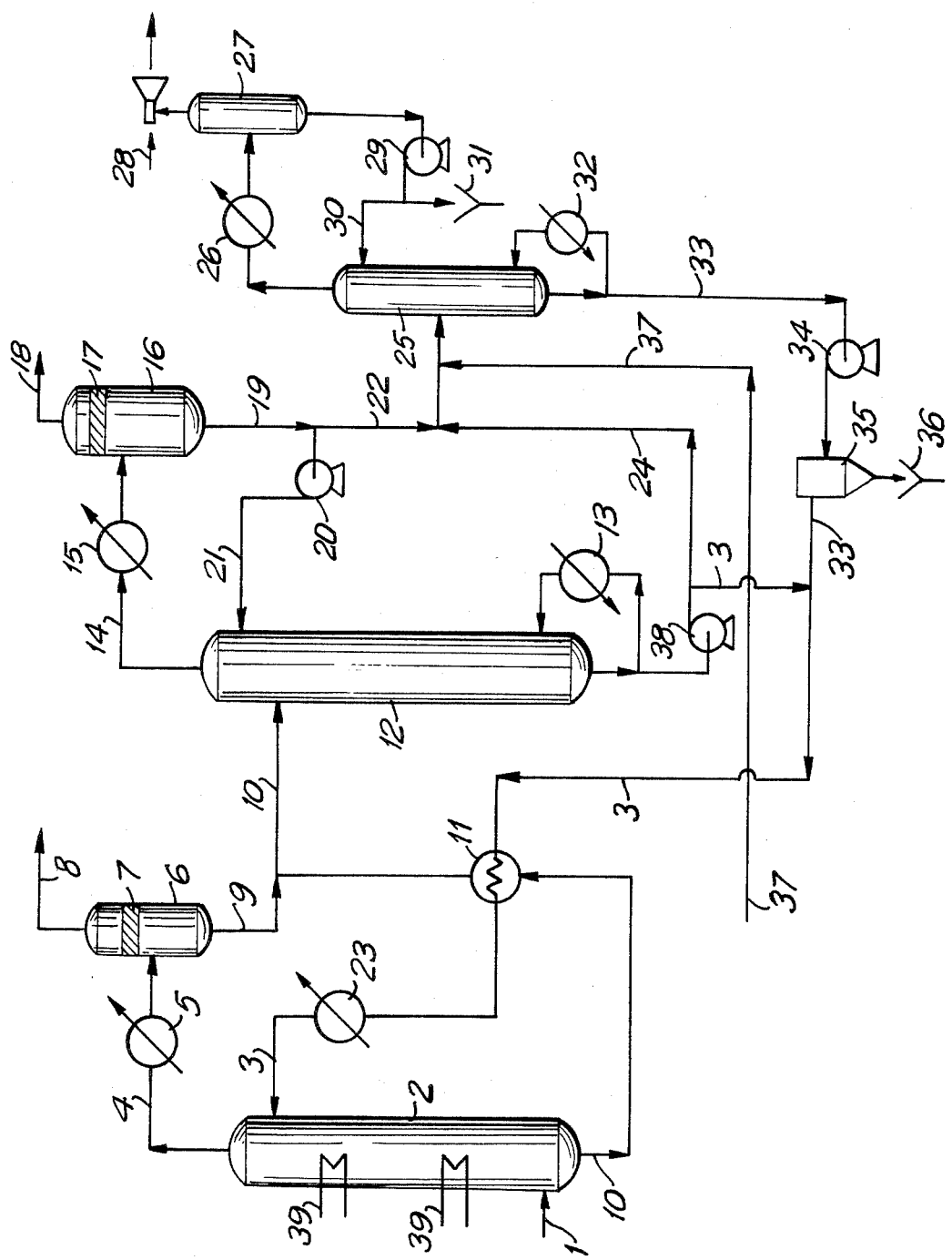

PROCESS OF SELECTIVE SEPARATION OF HYDROGEN SULFIDE FROM GASEOUS MIXTURES CONTAINING ALSO CARBON DIOXIDE

This is a continuation, of application Ser. No. 215,169 filed Dec. 11, 1980 now abandoned.

The instant invention relates to a process of separation of hydrogen sulfide from gaseous mixtures and more in particular to a process of selective separation of hydrogen sulfide from gaseous mixtures containing also carbon dioxide.

The selective removal of $H_2S$ is a problem widely felt in the petrochemical and oil industry and has not yet found an effective and economic solution.

Its possible applications are numerous and we mention by way of example the following main ones.

In the treatment of natural gas the removal of the $H_2S$ should be very thorough to the end of providing the users with a gas free from toxic or aggressive components. The $CO_2$ instead merely constitutes an inert component and might be left in the gas within the limits required by the specifications of calorific power and Wobbe number, hence avoiding the processing and respective costs involved with its separation.

In the treatment of the tail gases of Claus plants the sulfur compounds are reduced to $H_2S$, and if its removal were actually selective considerable savings would ensue.

In the preparation of industrial gases by synthesis, as with the synthesis of methanol, ammonia and synthetic fuel, it is very interesting to separate the $H_2S$ in a selective manner, in some cases in order to be enabled to utilize the $CO_2$, in other cases in order to feed the Claus plant with streams enriched with $H_2S$. The catalysts employed for said syntheses are in general very sensitive to sulfur compounds and there are required limits of the order of one part per million, else poisoning and deactivation of the catalyst occur within a short delay.

The processes adopted by the known art all are affected by problems of application which do not permit a really selective separation.

In practice the processes of the known art may be classified in three types, for the sake of simplifying explanation.

With the first type we may classify the processes based on the chemical absorption with aqueous solutions of tertiary amines.

Said processes owe their selectivity to the fact that the reaction of the $CO_2$ with the amines is much slower than the reaction of the $H_2S$, owing to the fact that the former reaction seems to require an intermediate reaction step of hydration of the $CO_2$.

This reaction results to be the limiting step.

From the difference of kinetics an advantage may be obtained by adopting such a lay out of the plant that while the $H_2S$ is substantially removed from the gases processed, the $CO_2$ is removed only in part.

Processes of this kind that use methyldiethanolamine in aqueous solution or a mixture of diisopropylamine, sulfolan and water, are industrially applicable.

However such processes do not allow a satisfactory treatment for the following reasons.

The gas processed remains considerably impure, the residual $H_2S$ may attain some hundreds of ppm, the selectivity of the separation diminishes much with pressure of operation and is strongly influenced by the operating conditions such as the composition and the flow rate of the gas to be processed, so as to make the plant not very suitable for operation at variable load.

Other similar processes based on the use of non-aminic absorbents, such as solutions of alkaline carbonates show a certain selectivity of separation but do not allow thorough purifications.

To the second type we may assign the processes based on the absorption with a solvent. Applicable industrial solvents are methanol and dimethyl ethers of polyethylene glycols, N-methyl pyrrolidone, alone or in mixtures with water.

It should be noted that generally speaking the processes of selective separation are just required when $H_2S$ is present in limited amounts namely when its partial pressure is low. In such conditions the acid "load" is low and the processes with a solvent are made nonadvantageous by the very thermodynamics and are not able to develop the best of their abilities, in that they require high flow rates of solvent and big apparatus equipment to obtain a thorough purification of the $H_2S$.

Moreover said solvents have the inconvenience of absorbing also the higher hydrocarbons and since they have, owing to the low acid "load", to operate with elevated circulation of solvent, the absorption of the hydrocarbons is complete in practice and this prevents the application of this kind of process to the case of heavy natural gases.

To the third type belong the oxidation processes based on the oxidation of the $H_2S$ yielding sulfur, such as the Gianmarco process or the Stretford process.

From the point of view of selectivity, said processes provide e excellent results, but there are strong counterindications from the ecologic point of view, such as the use of high amounts of arsenic or the production of sulfur in colloidal form with problems of separation and recovery not perfectly solved.

The process according to the instant invention makes it possible to overcome the inconveniences of the processes of the known art.

The process of the instant invention consists in separating selectively the hydrogen sulfide in the presence of carbon dioxide by chemical absorption with solutions of novel kind.

Said solutions consist in substantially anhydrous solutions of tertiary amines with an auxiliary organic solvent, in which the two components cooperate one as a reactant and the other one as a selective solvent.

As a matter of fact we have surprisingly found that also in the absence of water the $H_2S$ has a dissociation sufficient for its thorough separation, while the $CO_2$ mostly passes unaltered. Among the tertiary amines that can be employed alone or in mixtures with one another there are methyl diethanol amine, dimethyl ethanol amine, ethyl diethanol amine, diethyl ethanol amine, propyl diethanol amine, dipropyl ethanol amine, isopropyl diethanol amine, diisopropyl ethanol amine, methyl diiso propanol amine, ethyl diisopropanol amine, propyl diisopropanol amine, isopropyl diisopropanol amine, triethanol amine, N-methyl morfoline.

Among the solvents that can be employed alone or in mixtures with one another as components of the solution there are s ulfolan, N-methyl pyrrolidone, N-methyl-3-morfolone, the dialkylether monoethylene glycols, the dialkylether polyethylene glycols (where each of the alkyl groups contains 1 to 4 carbon atoms), the ethylene glycol, diethylene glycol, triethylene glycol, N-N-dimethyl formamide, N-formyl morfolin, N-N-dimethylimidazolidin-2-one and N-methylimidazole.

The ratio between the two components should be maintained in such a way that the tertiary amine be between 10% and 70% by weight and preferably between 20% and 50% by weight, of the overall mixture.

In the industrial application of the process attention will have to be paid to the fact that entrance of water into the cycle is possible, either as moisture of the gas fed, that will accumulate in the solvent, or as impurities in the components of the initial solution or of the make up solution. The removal of the water possibly introduced into the cycle may be carried out in a small concentrator that may operate periodically and/or on a reduced portion of the solvent in such a way as to dehydrate the solvent at the level wanted.

As a matter of fact the system in its industrial applications is able to tolerate without heavy modifications in operation a limited presence of Water content within the solution of absorption, in such a manner that the water content does not require particularly restrictive checking.

In the stage of regeneration the presence of limited amounts of water in the solvent may even be advantageous, since it generates steam in the column, which serves to strip the absorbed gases. In practice in the stripper the the aqueous reflux is vaporized, since the regenerated absorption solution is taken from the bottom in substantially anhydrous condition.

The water present in regeneration remains in a closed cycle in the stripper where it generates the bottom steam and constitutes the head reflux.

In industrial application the water content in the regenerated solution that is fed to the absorption step, is preferably limited to some unit percent by weight, while the fact remains true that the best selectivities are obtained with substantially anhydrous solutions in the absorption step.

By way of Example but without limitation, a flow sheet of embodiment of the process according to the invention will now be described with reference to FIG. 1.

By means of the piping 1 the gas to be processed is fed to the absorption column 2, to which is fed with the piping 3 the absorption solution.

Within the column 2, that may be a plate column or a packed column of conventional type, there flow in countercurrent the gas to be processed and the absorption solution that selectively removes the $H_2S$.

From the top of column 2 there is taken the processed gas by means of the piping 4; the processed gas is cooled in the cooler 5 and the traces of solvent so condensed are collected in the vessel 6 equipped with a demister 7. The gas so processed is discharged from the plant and is sent to utilization by means of the piping 8, while the traces of solvent recovered are sent to the recuperation column with the piping 9.

The "loaded" absorption solution is discharged from column 2 by means of the piping 10, is preheated by exchange with the exhausted recycle solution in the exchanger 11, and is fed then to the recuperation column 12.

In column 12 the "loaded" absorption solution is subjected to stripping, reversing by heat action the absorption reaction carried out in 2.

Heat is furnished in the boiler 13, and the acid gases constituted by the $H_2S$ absorbed by the solution in the column 2 rise in the stripper and by way of the piping 14 they are fed to the cooler 15 wherein there is condensed the portion of solution vaporized to carry out the stripping, that is then separated in the barrel 16, equipped with the demister 17. From the piping 18 there is discharged the $H_2S$ removed from the gases processed, that is then sent to conventional recuperation stages.

By means of the piping 19, the pump 20 and the pipe 21, the solution recovered in 16, which has a water content higher than the absorption solution, is refluxed to the stripping. Alternatively, a part of it is sent through 22 to the operations of successive purification of the solution.

From the bottom of the stripper 12 the regenerated solution is sent back to column 2 by means of the line 3 after previous heat exchange in 11 and cooling in 23.

Through the piping 24, a part of the solvent may be sent, in case there is dilution of the solution, to the concentrating column 25 equipped with a condenser 26, with a reflux accumulator 27, with a vacuum system 28 and with a reflux and discharge pump 29.

The reflux is effected through 30 and the discharge through 31.

The necessary heat is provided with the boiler 32.

With the piping 33 and the pump 34, after previous separation of possible solids separated in the separator 35 and discharge 36, the purified solvent is recycled.

The line 37 is utilized for the introduction into the cycle of the loading or integrating solvent.

The pump 38 ensures the recycle between the stripper 12 and the absorber 2.

In the case in which a strict checking of the reaction temperatures in the column 2 were required, there are to be provided intermediate supplemental coolers indicated with 39.

In order better to make clear the gist and scope of the invention, some experimental tests are reported hereinafter.

EXAMPLE 1

In a column of internal diameter 50 mm and 2.50 meters high, equipped with plates and bubble-caps, operation was carried out at a pressure of 30 kg/cm$^2$ and at 40° C.

The gas to be processed was constituted by $CH_4$ for 95.6% by volume, while the $CO_2$ was 4.0% by volume and the $H_2S$ was 0.4% by volume.

The absorption solution was constituted by methyl diethanol amine for 35% by weight and by sulfolan for 65% by weight.

The gas flow rate was 3.45 Ncm/h while the liquid flow rate was 6 kg/h.

From the head of the column, gas with 5 ppm of $H_2S$ was obtained.

The absorbing solution discharged from 10 was fed to a stripping column of 80 mm diameter, height 1?5 metres, equipped with bubble-cap plates, operating at an absolute pressure of 100 mm Hg.

The gas obtained at the head was composed of $H_2S$ for 42.5% by volume and of $CO_2$ for 57.5% by volume.

The abatement of the $H_2S$ resulted to be 99.9% while the $CO_2$ resulted to be 13.5%.

The selectivity of abatement therefore is 7.4 times favourable to $H_2S$.

EXAMPLE 2

In the same conditions of the Example 1 an absorption solution was employed that was constituted by 26% of dimethyl ethanol amine and by 74% of N-methyl pyrrolidone, by weight.

The selectivity of abatement was 7.0 times although always the content of $H_2S$ of the gases processed was lower than 10 ppm.

EXAMPLE 3

In the same conditions of the preceding Example there was employed an absorption solution constituted by 35% by weight of diethyl ethanol amine and by 65% by weight of formyl morfoline.

The selectivity of abatement was 7.2 times.

EXAMPLE 4

The solvent adopted is constituted by 35% by weight of N-methyl morfoline and by 65% by weight of N-methyl-3-morfolone. In this case the flow rate of gas was 4.065 Ncm/h and the regeneration was operated at atmospheric pressure. The other conditions are the same as in Example 1. The selectivity of abatement was 7.1 times.

EXAMPLE 5

In the apparatus of Example 1 operation was carried out with gas containing 8% by volume of $CO_2$, 0.8% by volume of $H_2S$ and the remainder of 100% being $CH_4$.

The temperature was 60° C. and the pressure was 15 $kg/cm_{abs}^2$.

Feeding 1.3 Ncm/h of gas in countercurrent to 6 kg/h of a mixture of absorption constituted by methyl diethanol amine of 15% by weight, by diethyl ethanol amine of 20% by weight, by sulfolan of 50% by weight and by N-methyl-pyrrolidone of 15% by weight.

The content of $H_2S$ in the gases treated, was 8 ppm, while the selectivity of abatement resulted to be 7.6 times.

EXAMPLE 6

A synthetic mixture constituted by 25.1% by volume of CO, by 69.9% by volume of $H_2$ and containing 4.9% by volume of $CO_2$ and by 0.1% by volume of $H_2S$, was subjected to processing according to the conditions said in Example 1.

From the head of the column a gas was obtained that contained $H_2S$ by 2 ppm while the residual $CO_2$ remains 3.68% by volume.

The factor of selectivity is 4.8 times.

By way of comparison there follow Examples with an absorption solution containing small percentages of water.

EXAMPLE 7

In the apparatus of Example 1 operation was carried out in the same operating conditions with the same absorption solution to which 3% by weight of water had been added.

From the stripping column, operating at atmospheric pressure and with a temperature at the bottom of the column of 145° C., a head gas was obtained constituted by 35.3% by volume of $H_2S$ and by 64.7% by volume of $CO_2$.

The abatement of the $H_2S$ resulted to be 99.9% whilst the $CO_2$ resulted with 18.4%.

The selectivity of abtamente resulted to be 5.4 times favourable to $H_2S$.

EXAMPLE 8

In the apparatus of Example 1 operation was carried out in the same conditions of operation with the same absorption solution, to which 8% by weight of water had been added.

From the stripping column, operating at atmospheric pressure and at a temperature at the bottom of the column of 135° C., a head gas was obtained that was constituted by 32% by volume of $H_2S$ and by 68% by volume of $CO_2$.

The abatement of the $H_2S$ resulted to be 99.9% whilst for $CO_2$ the result was 20.3%.

The selectivity of abatement resulted to be 4.9 times favourable to $H_2S$.

We claim:

1. A process for selective separation of hydrogen sulfide from gaseous mixtures containing carbon dioxide by selective absorption with a substantially anhydrous solution consisting essentially of:
    (a) a tertiary amine selected from the group consisting of methyl diethanol amine, dimethyl ethanol amine, ethyl diethanol amine, diethyl ethanol amine, propyl diethanol amine, dipropyl ethanol amine, isopropyl diethanol amine, di-isopropyl ethanol amine, methyl di-isopropanol amine, ethyl di-isopropanol amine, propyl di-isopropanol amine, triethanol amine, N-methyl morphaline and mixtures thereof; and
    (b) an organic solvent selected from the group consisting of sulfolane, N-methyl-pyrrolidone, N-methyl-3-morpholone, di-e-mono ($C_1$-$C_4$) alkylether-monoethylene glycol, di-e-mono ($C_1$-$C_4$) alkylether-polyethylene glycol, ethylene glycol, diethylene glycol, triethylene glycol, N,N-dimethylformamide, N-formyl-morpholine, N,N-dimethylimidazolidin-2-one, N-methyl-imidazole and mixtures thereof,
    said tertiary amine being present in an amount between 10 and 70 percent by weight of the total solution and water present in the solution being less than 2 percent by weight of the total solution and selectively absorbing hydrogen sulfide.

2. The process of claim 1 wherein the tertiary amine is present in an amount between 20 and 50 percent by weight of the total solution.

3. The process of claim 1 wherein the absorption is carried out at a temperature between 10° and 80° C.

4. The process of claim 3 wherein the absorption is carried out at a temperature between 40° and 60° C.

* * * * *